United States Patent
Curry (10) Patent No.: US 8,906,210 B2
(45) Date of Patent: Dec. 9, 2014

(54) FLUX LIMITING MEMBRANE FOR INTRAVENOUS AMPEROMETRIC BIOSENSOR

(75) Inventor: Kenneth M. Curry, Oceanside, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 13/491,222

(22) Filed: Jun. 7, 2012

(65) Prior Publication Data

US 2013/0150690 A1    Jun. 13, 2013

Related U.S. Application Data

(63) Continuation of application No. 11/710,329, filed on Feb. 23, 2007, now abandoned.

(60) Provisional application No. 60/777,139, filed on Feb. 27, 2006.

(51) Int. Cl.
*G01N 33/487* (2006.01)
*A61B 5/1486* (2006.01)
*A61B 5/145* (2006.01)

(52) U.S. Cl.
CPC ......... *A61B 5/14865* (2013.01); *A61B 5/14532* (2013.01)
USPC ............ 204/403.01; 204/403.02; 204/403.03; 204/403.05; 205/777.5; 205/778

(58) Field of Classification Search
USPC .............. 204/403.01–403.15; 205/777.5–778
See application file for complete search history.

(56) References Cited

U.S. PATENT DOCUMENTS

| 4,314,905 A | 2/1982 | Etzel et al. |
| 4,542,291 A | 9/1985 | Zimmerman |
| 4,661,105 A | 4/1987 | Gale |
| 4,937,444 A | 6/1990 | Zimmerman |
| 4,952,406 A | 8/1990 | Brown et al. |
| 5,273,756 A | 12/1993 | Fallon et al. |
| 5,326,413 A * | 7/1994 | Esemplare et al. ........... 156/154 |

(Continued)

FOREIGN PATENT DOCUMENTS

| WO | 2005/074612 A2 | 8/2005 |
| WO | 2006017358 A1 | 2/2006 |
| WO | 2006/050033 A2 | 5/2006 |

OTHER PUBLICATIONS

Renard, Implantable Glucose Sensors for Diabetes Monitoring, Minimum Invasive Ther. Allied Technol., vol. 13, No. 2, pp. 78-86, 2004.

(Continued)

*Primary Examiner* — Bach Dinh
(74) *Attorney, Agent, or Firm* — Michael Crapenhoft (57) ABSTRACT

A flux limiting layer for an intravenous amperometric biosensor is formed on a substrate to limit a diffusion rate of an analyte from blood to an enzyme electrode. The layer may be formed from ethylene vinylacetate (EVA) dissolved in a solvent such as paraxylene, spray-coated to cover a portion of the electrode, and cured to seal the electrode to the substrate. In a glucose sensor having glucose oxidase disposed on the electrode, thickness and concentration of the EVA layer are optimized to promote a linear output of electrode current as a function of blood glucose concentration.

20 Claims, 5 Drawing Sheets

(56) References Cited

U.S. PATENT DOCUMENTS

| | | | |
|---|---|---|---|
| 5,423,883 A | 6/1995 | Helland | |
| 5,494,562 A | 2/1996 | Maley et al. | |
| 5,788,983 A * | 8/1998 | Chien et al. | 424/449 |
| 5,837,454 A * | 11/1998 | Cozzette et al. | 435/6.11 |
| 5,838,546 A | 11/1998 | Miyoshi | |
| 5,882,494 A * | 3/1999 | Van Antwerp | 600/347 |
| 5,987,361 A | 11/1999 | Mortimer | |
| 6,124,397 A * | 9/2000 | Smith | 524/832 |
| 6,454,710 B1 | 9/2002 | Ballerstadt et al. | |
| 6,833,612 B2 | 12/2004 | Kinsman | |
| 6,885,107 B2 | 4/2005 | Kinsman | |
| 6,940,141 B2 | 9/2005 | Kinsman | |
| 6,956,295 B2 | 10/2005 | Kinsman | |
| 6,964,886 B2 | 11/2005 | Kinsman | |
| 6,972,423 B2 | 12/2005 | Welland et al. | |
| 6,985,764 B2 | 1/2006 | Mason et al. | |
| 7,122,390 B2 | 10/2006 | Kinsman | |
| 2003/0088166 A1 * | 5/2003 | Say et al. | 600/345 |
| 2004/0224001 A1 * | 11/2004 | Pacetti et al. | 424/423 |
| 2005/0154374 A1 | 7/2005 | Hunter et al. | |
| 2005/0197554 A1 * | 9/2005 | Polcha | 600/365 |
| 2005/0272989 A1 | 12/2005 | Shah et al. | |
| 2006/0046275 A1 * | 3/2006 | Collier et al. | 435/7.9 |

OTHER PUBLICATIONS

J. Wang, Glucose Biosensors: 40 Years of Advances and Challenges, Electroanalysis, vol. 13, No. 12, pp. 983-988, 2001.
International Preliminary Report on Patentability, Sep. 2, 2008, PCT/US2007/004828.
Chinese Office Acton, Apr. 26, 2010.
Chinese Office Action, Mar. 9, 2011.

\* cited by examiner

FLUX LIMITING MEMBRANE FOR INTRAVENOUS AMPEROMETRIC BIOSENSOR

CLAIM OF PRIORITY

The present application for patent is a continuation of U.S. patent application Ser. No. 11/710,329, filed Feb. 23, 2007, entitled Flux Limiting Membrane for Intravenous Amperometric Biosensor and it also claims priority to Provisional Application No. 60/777,139 filed Feb. 27, 2006, entitled Membrane Useful for Glucose Measurements and assigned to the assignee hereof and hereby expressly incorporated by reference herein.

FIELD OF THE INVENTION

The invention relates to amperometric biosensors for measuring blood chemistry. In particular, the invention relates to an intravenous sensor for measuring a biological parameter such as blood glucose concentration.

BACKGROUND

Amperometric biosensors are known in the medical industry for analyzing blood chemistry. Early biosensors, also known as enzyme electrodes, were first proposed by Clark and Lyons and implemented by Updike and Hicks. Enzyme electrodes typically include an oxidase enzyme, such as glucose oxidase, that is immobilized behind a dialysis membrane at the surface of an electrode. In the presence of blood, the membrane selectively passes an analyte of interest, e.g. glucose, to the oxidase enzyme where it undergoes oxidation or reduction, e.g. the reduction of oxygen to hydrogen peroxide. Amperometric biosensors function by producing an electric current when a potential sufficient to sustain the reaction is applied between two electrodes in the presence of the reactants. For example, in the reaction of glucose and glucose oxidase, the hydrogen peroxide reaction product may be subsequently oxidized by electron transfer to an electrode. The resulting flow of electrical current in the electrode is indicative of the concentration of the analyte of interest.

Applications for amperometric biosensors include measuring analytes in blood-borne gases, electrolyte levels in blood and in particular, blood glucose concentration. For measuring glucose, subcutaneous methods have been proposed. For example, see Renard, "Implantable Glucose Sensors for Diabetes Monitoring," Minim Invasive Ther Allied Technol, Vol. 13, No. 2, pp. 78-86 (2004). While these minimally invasive glucose monitoring systems properly display trends in plasma glucose concentration, they do not track glucose accurately enough to be used for intensive insulin therapy, for example, where inaccuracy at conditions of hypoglycemia could pose a very high risk to the patient. In addition, sensors based upon the enzyme glucose oxidase need to have access to adequate oxygen to provide a linear glucose response. Sensor systems optimized for subcutaneous tissue would not necessarily function well in venous blood, where oxygen tension can be 20 mm Hg or less.

At the present time, the most reliable way to obtain a highly accurate blood glucose measurement in an ICU patient is by a direct time-point method, which involves drawing a blood sample and sending it off for laboratory analysis. This is a time-consuming method that is often incapable of producing needed results in a timely manner. Despite ongoing research in this field, many improvements in glucose monitoring are still needed.

One of the difficulties impeding the development of an intravenous amperometric sensor is that the sensor must be small enough to be suspended within a blood vessel, but robust enough to immobilize an enzyme so that a reaction may be sustained for a sufficient length of time. An intravenous sensor must also be biocompatible, such that it does not release any toxins into a patient, and when implanted, e.g. through a catheter in a femoral vein, discourages clotting of blood at the membrane surface that would prevent plasma from diffusing to the enzyme layer.

SUMMARY

The invention discloses a biocompatible flux limiting membrane for an amperometric biosensor designed for intravenous use and continuous analyte monitoring. The flux limiting membrane may be formed on a sensor electrode that is at least partially coated with a reagent selected to react with a substance found in blood. The flux limiting membrane limits a rate at which the substance diffuses through the flux limiting membrane to react with the reagent. The flux limiting membrane may include an ethylene vinylacetate (EVA) polymer selected for its biocompatibility, adhesion, physical, and diffusion properties. In one embodiment, the membrane may include one or more cured layers of EVA that are applied by spraying a solution having a percentage of EVA dissolved in paraxylene.

An intravenous amperometric biosensor may be formed using the EVA membrane as a flux limiting layer to at least partially cover the surface of an enzyme electrode. The biosensor may be formed on a flex circuit substrate having reference, counter, and working electrodes mounted thereon, wherein one working electrode may be the enzyme-bearing electrode. In one embodiment, the biosensor may be a glucose sensor, the working electrode may be at least partially coated with glucose oxidase, and an EVA membrane may be formed on the working electrode to provide a flux limiting barrier that selectively allows diffusion of oxygen and glucose from blood to the glucose oxidase. Adhesive properties of EVA mechanically seal the glucose oxidase to the electrode and the electrode to the substrate to improve mechanical integrity during intravenous insertion. The composition of the EVA membrane may be optimized such that, when the biosensor is located intravenously with the working electrode energized, the current output of the working electrode is a linear function of blood glucose concentration.

A related method is also disclosed for forming a flux limiting layer on an enzyme electrode that is bonded to a substrate of an amperometric biosensor. The method may include dissolving EVA in a solvent such as paraxylene, applying a layer of the dissolved EVA to an area of the substrate that includes at least a portion of the enzyme electrode, and curing the applied layer. The EVA may be dissolved in paraxylene to facilitate application by spray-coating, and the thickness and concentration of the EVA membrane may be optimized to promote a linear output of electrode current as a function of blood glucose concentration.

BRIEF DESCRIPTION OF THE DRAWINGS

The features, objects, and advantages of the invention will become more apparent from the detailed description set forth below when taken in conjunction with the drawings, wherein.

DETAILED DESCRIPTION

The invention discloses an adhesive biocompatible polymer for forming a flux-limiting membrane on an enzyme-bearing electrode in an intravenous amperometric biosensor. When the sensor is installed in a patient to measure blood chemistry, the membrane improves sensor accuracy by allowing oxygen to pass from the blood to the sensor while limiting the passage of larger molecules. The biocompatibility of the membrane limits the number of toxins that may be introduced into the bloodstream, and the adhesive properties enhance the mechanical integrity of the sensor during installation and operation.

In one embodiment, the membrane may be used on a glucose sensor for limiting the amount of glucose flux from blood to the sensor electrode. The biocompatible polymer that forms the membrane may contain an optimized content of dissolved ethylene vinylacetate (EVA). A solvent such as paraxylene may be used to dissolve the EVA into a solution suitable for application to the electrode by spray-coating or other means.

EVA is selected for its many properties that are advantageous for forming a flux limiting membrane. EVA is a biocompatible, linear polymer. Formed as a membrane layer on a biosensor electrode, it can provide a general hydrophobic property to accentuate oxygen transport, but with sufficient hydrophilic segments to still allow for limited glucose transport. This is important in intravenous applications, where glucose is in preponderance in the blood plasma in comparison to free oxygen molecules. Thus, an EVA membrane may provide a desired diffusion barrier that passes an abundance of oxygen while restricting the passage of glucose. In addition, an EVA polymer as applied herein may provide a mechanically strong adhesive for coating an enzyme-bearing electrode on a flex circuit substrate suitable for long-term continuous intravenous use. Also, films of EVA are very elastomeric, which is important in a situation where the electrode may need to navigate a tortuous path, for example, into venous anatomy. Moreover, the concentration of EVA and the thickness of the applied layers may be controlled in the manufacturing process to promote a linear output of electrode current as a function of blood glucose concentration.

One application for a flux limiting membrane is in a thin-film amperometric biosensor formed on a flex circuit. Flex circuits have been applied in medical devices as microelectrode substrates for in vivo applications. For example, one flex circuit design uses a laminate of a conductive foil (e.g., copper) on a flexible dielectric substrate (e.g., polyamide). The flex circuit may be formed on the conductive foil using masking and photolithography techniques. Flex circuits are desirable due to their low manufacturing cost, ease in design integration, and physical flexibility during transport in applications such as central venous catheter (CVC) insertion.

Figure 1:
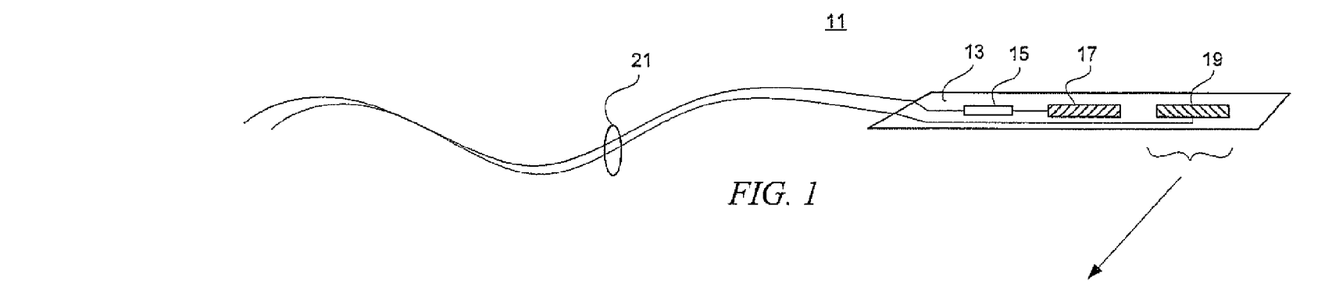
FIG. 1 shows an amperometric biosensor in the form of a flex circuit having a working electrode coated with a flux limiting membrane according to an embodiment of the invention.

FIG. 1 is an amperometric biosensor 11 in the form of a flex circuit that incorporates a flux limiting membrane according to an embodiment of the invention. The biosensor or sensor 11 may be formed on a substrate 13 (e.g., a flex substrate). One or more electrodes 15, 17 and 19 may be attached or bonded to a surface of the substrate 13. The biosensor 11 is shown with a reference electrode 15, a counter electrode 17, and a working electrode 19. In another embodiment, one or more additional working electrodes may be included on the substrate 13. Electrical wires 21 may transmit power to the electrodes for sustaining an oxidation or reduction reaction, and may also carry signal currents to a detection circuit (not shown) indicative of a parameter being measured. The parameter being measured may be any analyte of interest that occurs in, or may be derived from, blood chemistry. In one embodiment, the analyte of interest may be hydrogen peroxide, formed from reaction of glucose with glucose oxidase, thus having a concentration that is proportional to blood glucose concentration.

Figure 2:
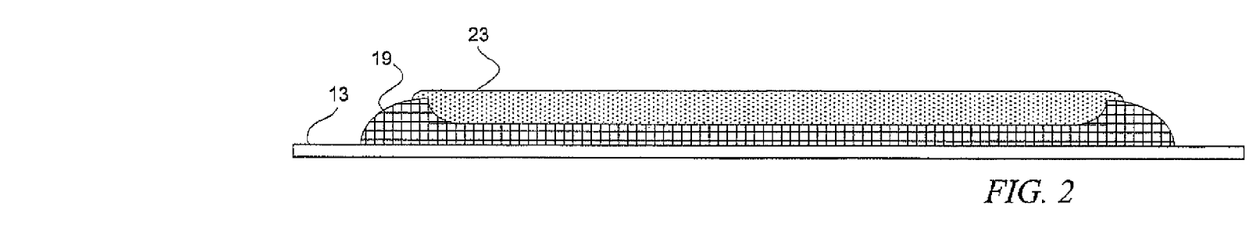
FIG. 2 is a magnified side cross-sectional view of the working electrode portion of the biosensor of FIG. 1, shown prior to application of a flux limiting membrane according to an embodiment of the invention.

The magnified cross-sectional side view of FIG. 2 shows a distal portion of the substrate 13 in the vicinity of the working electrode 19. The working electrode 19 may be at least partially coated with a reagent or enzyme layer 23 that is selected to chemically react when the sensor is exposed to certain reactants found in the bloodstream. For example, in an embodiment for a glucose biosensor, enzyme layer 23 may contain glucose oxidase, such as may be derived from Aspergillus niger (EC 1.1.3.4), type II or type VII.

To promote a reaction of the enzyme with blood, the enzyme layer 23 may be formed within a matrix that is active on its surface. This may be achieved, for example, by adding or cross-linking the enzyme to an active hydrogel. The hydrogel layer may be water absorbent, and swell to provide active transport of a reactant in the blood (e.g. glucose) from the blood to the enzyme. Intermolecular bonds may be formed throughout the hydrogel layer to create adhesion and a density of matrix to allow for even dispersion of the reagent across the hydrogel surface and throughout the hydrogel layer. Reaction products may then be communicated to the electrode layer.

Figure 3:
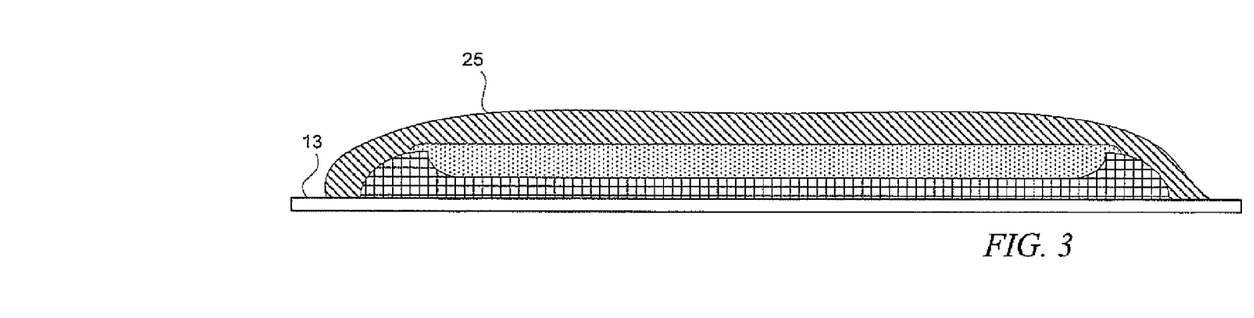
FIG. 3 is a magnified cross-sectional view of the working electrode portion of the biosensor of FIG. 1, shown after application of the flux limiting membrane according to an embodiment of the invention.

FIG. 3 shows a magnified cross sectional side view of the working electrode site on the sensor substrate 13. A flux limiting membrane 25 is added onto the enzyme layer 23, such that the membrane 25 at least partially covers the enzyme layer 23. With the sensor 11 installed in an intravenous location, the flux limiting membrane 25 may selectively allow diffusion, from blood to the enzyme layer 23, a blood component that reacts with the enzyme. In a glucose sensor embodiment, the flux limiting membrane 25 passes an abundance of oxygen, and selectively limits glucose, to the enzyme layer 23. In addition, a flux limiting membrane 25 that has adhesive properties may mechanically seal the enzyme layer 23 to the working electrode 19, and may also seal the working electrode 19 to the sensor substrate 13. It is herein disclosed that a flux limiting membrane formed from an EVA polymer may serve as a flux limiter at the top of the electrode, but also serve as a sealant or encapsulant at the enzyme/electrode boundary and at the electrode/substrate boundary. An additional biocompatible layer (not shown), including a biocompatible anti-thrombotic substance such as heparin, may be added onto the flux limiting membrane 25.

The sensor 11 works on an amperometric measurement principle, where the working electrode 19 is held at a positive potential relative to the counter electrode 17. The positive potential is sufficient to sustain an oxidation reaction of hydrogen peroxide, which is the result of a glucose reaction with the glucose oxidase. Thus, the working electrode 19 functions as an anode, and collects electrons produced at the surface of the working electrode 19 that result from the oxidation reaction. The collected electrons flow into the working electrode 19 as an electrical current. In one embodiment with the working electrode coated with glucose oxidase, the oxidation of glucose produces a hydrogen peroxide molecule for every molecule of glucose, when the working electrode 19 is held at a potential between about +450 mV and about +650 mV. The hydrogen peroxide produced oxidizes at the surface of the working electrode 19 according to the equation:

$$H_2O_2 \rightarrow 2H^+ + O_2 + 2e^-$$

The equation indicates that two electrons are produced for every hydrogen peroxide molecule oxidized. Thus, under certain conditions, the amount of electrical current may be proportional to the hydrogen peroxide concentration. Since one hydrogen peroxide molecule is produced for every glucose molecule oxidized at the working electrode, a linear relationship may exist between the blood glucose concentration and the resulting electrical current. The reader may refer to the following article for additional information on electronic sensing theory for amperometric glucose biosensors: J. Wang, "Glucose Biosensors: 40 Years of Advances and Challenges," Electroanaylsis, Vol. 13, No. 12, pp. 983-988 (2001).

To achieve the linear relationship or substantially linear relationship, the working electrode 19 is designed to promote the desired chemical reactions. In the amperometric sensor 11, the chemistry may be controlled by applying one or more membranes, or layers, of varying composition on the surface of a flex circuit substrate. In one embodiment, the substrate 13 may be a polyimide material, the enzyme layer 23 may be a cross-linked hydrogel, and the flux limiting layer 25 may be an EVA polymer according to an embodiment of the invention. EVA is selected, inter alia, for its adhesive and biocompatible qualities in polymeric implant devices for controlling drug delivery rates.

The substrate 13 provides an insulated structure for mounting the electrodes and membrane layers. In one embodiment, the substrate 13 may be between about 0.050 and 0.060 inches wide and between about 1.0 and 2.0 inches long. The thickness of the membrane layers may vary between about 0.5 microns and about 10 microns. In one embodiment, one or more of the flux limiting membrane layers may have a thickness in the about 0.5 micron to about 10 micron range.

The electrical wires 21 may be coupled or soldered to conductive traces formed on the substrate 13 using flex circuit technology. For example, the traces may be gold-plated copper. In one embodiment, the sensor 11 may be designed so that the flex circuit terminates to a tab that mates to a multi-pin connector, such as a 3-pin, 1 mm pitch ZIF Molex connector. Such a connection facilitates excitation of the working electrode and measurement of electrical current signals, for example, using a potentiostat or other controller.

The electrodes 15, 17 and 19 may be applied to the substrate 13 using a thick film process and commercially available inks. In one embodiment, the reference electrode 15 may be a silver/silver chloride type deposited or formed on the substrate 13. The reference electrode 15 establishes a fixed potential from which the potential of the counter electrode 17 and the working electrode 19 may be established. The reference potential is Nernstian. For the silver/silver chloride electrode, the reference potential is maintained by the following half-reaction:

$$Ag^0 \rightarrow Ag^+ + e^-$$

The counter electrode 17 may be constructed from conductive materials such as platinum or graphite. These materials may be formulated as an ink for application to the substrate 13 using a thick film process and cured accordingly. The counter electrode 17 provides a working area for conducting the majority of electrons produced from the oxidation chemistry back to the blood solution. Otherwise, all the current would likely pass through the reference electrode 15, and may reduce its service life. In one embodiment, the counter electrode 17 may be formed with a surface area greater than that of the working electrode 19.

The working electrode 19 may be formed using platinum/graphite materials similar to those used for forming the counter electrode 17. In other embodiments, the working electrode 19 may be formed from other conductive materials. Its operation has been described thus far as promoting anodic oxidation of hydrogen peroxide at its surface. Other embodiments are possible, for example, the working electrode 19 may be held at a negative potential. In this case, the electrical current produced at the working electrode 19 may result from reduction of oxygen.

In one embodiment, the biosensor 11 may be installed within a probe or catheter for intravenous insertion into a patient, for example, via a CVC. The biosensor 11 may function as an amperometric sensor while immersed in a patient's bloodstream by the addition of an enzyme-bearing hydrogel layer 23 to a surface of the working electrode 19. The hydrogel layer 23 may be sealed to the working electrode 19, and the working electrode 19 may be sealed to the substrate 13, by using the flux limiting layer 25. That is, in addition to its diffusion function, the flux limiting layer 25 also serves to bond the hydrogel and electrode firmly to the substrate 13.

Figure 4:
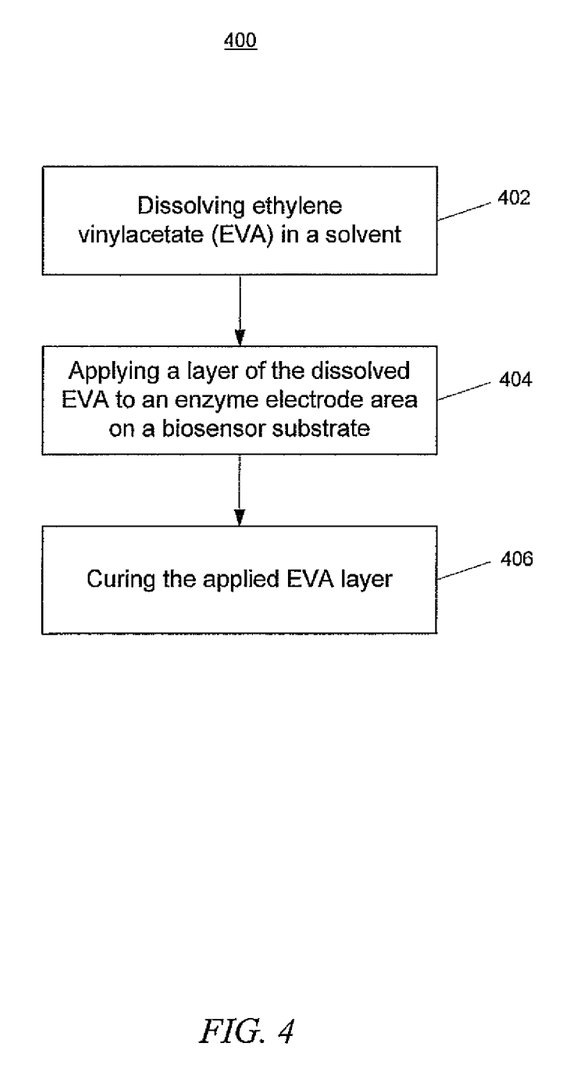
FIG. 4 is a process flow chart illustrating steps for forming a flux limiting membrane on a biosensor substrate according to an embodiment of the invention.

Based on experimental trials, the substance of which is disclosed in sections that follow, a method has been developed and is herein disclosed as a series of process steps forming a flux limiting EVA membrane on a biosensor electrode. FIG. 4 illustrates one such embodiment of a method 400.

Method 400 includes step 402, in which EVA is dissolved in a solvent. The EVA may be provided from a source having a composition anywhere from about 9 wt % vinyl acetate (EVA-9) to about 40 wt % vinyl acetate (EVA-40). The solvent should be chosen for its ability to dissolve EVA, to promote adhesion to the biosensor substrate and enzyme electrode, and to form a solution that may be effectively applied (e.g. spray-coated). Solvents such as cyclohexanone, paraxylene, and tetrahydrofuran may be suitable for this purpose. In this step, the solution may include about 0.5 wt % to about 6.0 wt % of the EVA composition. In addition, the solvent is sufficiently volatile to evaporate without undue agitation to prevent issues with the underlying enzyme, but not so volatile as to create problems with the spray process.

Step 404 involves applying a layer of the EVA solution to an area of the biosensor substrate to at least partially coat the enzyme electrode. In one embodiment, step 404 may include completely coating the enzyme electrode and sealing the electrode to the biosensor substrate. Step 404 may be performed, for example, by spraying the EVA solution onto the enzyme electrode area of the substrate 13 to form a layer having a uniform or near uniform thickness. Additional layers may be added in this step to achieve a desired membrane thickness. Layers of EVA solution formed in this step may also be applied by brushing, immersion, or similar technique.

In step 406, the applied EVA layer or layers are cured to form the flux limiting membrane. This step may be performed by drying in ambient air, by curing in a low-temperature oven (between about 30 and about 40 degrees C.), or alternatively, by annealing at a temperature between about 50 and 65 degrees C. (preferably, slightly below 65 degrees C.), which is the softening temperature region of EVA. An additional step may be added to method 400, in which the cured flux limiting membrane is coated with a biocompatibility layer composed of a biocompatible material such as heparin.

Using method 400, a population of eight prototype sensors was fabricated with flux limiting layers and each sensor was tested for glucose response. The prototype sensors were denoted G1, G2, G3, G5, G6, G7, G8 and G9. Each sensor was fabricated on a flex circuit configured with a platinum/graphite working electrode and a silver/silver chloride reference electrode. A recess was formed in the working electrode and filled with a glucose oxidase enzyme layer. A 2.0 wt % solution of EVA-40 was prepared by dissolving in tetrahydrofuran (THF). The working electrode area of each sensor was then coated with a flux limiting layer by dipping the electrode in the EVA solution one or more times and allowing the coating to cure. Curing was performed either by air-drying at ambient temperature or by oven-curing at about 59 degrees C. for ten minutes. The table below indicates how each prototype sensor was made, where the value under L indicates the number of times (1× or 3×) each sensor was dipped in the EVA solution to coat the working electrode, and the value under T indicates whether the sensor was cured in ambient air (0) or in a 59-degree C. oven for ten minutes (59/10).

| SENSOR | L | T |
|---|---|---|
| G1 | 3× | 0 |
| G2 | 1× | 59/10 |
| G3 | 1× | 0 |
| G5 | 3× | 0 |
| G6 | 1× | 59/10 |
| G7 | 1× | 0 |
| G8 | 3× | 59/10 |
| G9 | 3× | 59/10 |

Figure 5:
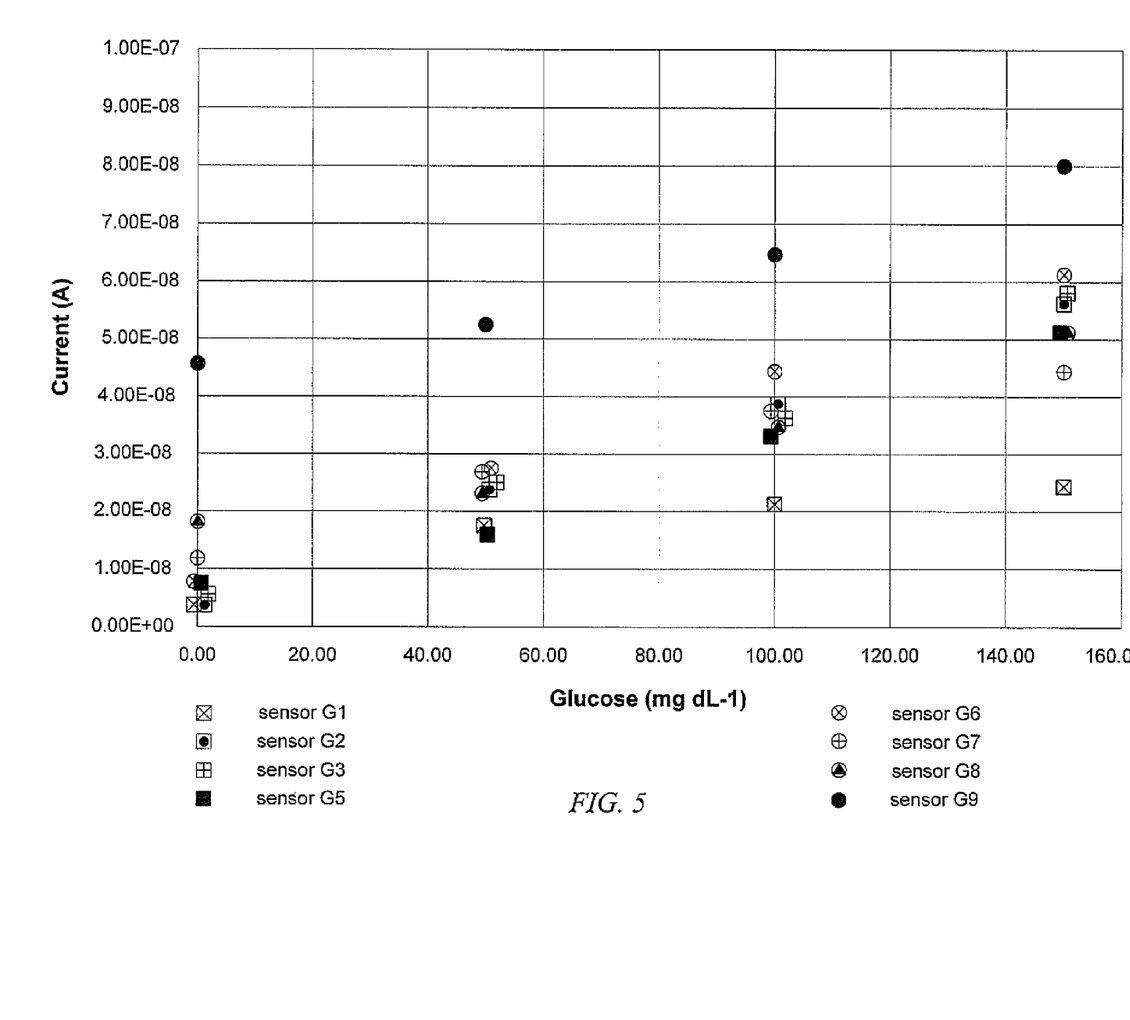
FIG. 5 is a graph of current output vs. glucose concentration for biosensors formed with flux limiting membranes according to an embodiment of the invention.

FIG. 5 shows the results of a glucose assay performed on each prototype sensor to determine the linearity of response. Each sensor was exposed to a solution of known glucose concentration, and its working electrode excited at a potential of about 650 mV. The resulting electrical current output in amperes in the working electrode was then measured and plotted versus glucose concentration in mg/dL. For each sensor, the current output was measured at four values of glucose concentration: 0.00, 50.00, 100.00, and 150.00 mg/dL.

A linear regression technique was applied to the test data to derive a slope for a theoretical line through each group of four data points, and to determine the linearity of response. The coefficient of multiple determination, $r^2$, was computed for each sensor to determine the adequacy of the linear regression model, where $$r^2 = SSR/SST$$

and where SSR represents the sum of squares due to regression, and SST represents the total sum of squares. The results are tabulated below:

| SENSOR | SLOPE | $r^2$ |
|---|---|---|
| G1 | 1.24E−10 | 0.8563 |
| G2 | 3.42E−10 | 0.9994 |
| G3 | 3.37E−10 | 0.9998 |
| G5 | 2.95E−10 | 0.9813 |
| G6 | 3.44E−10 | 0.9981 |
| G7 | 2.11E−10 | 0.9581 |
| G8 | 2.21E−10 | 0.9480 |
| G9 | 2.28E−10 | 0.9701 |

The results indicate excellent linearity, with $r^2$ values for eight prototype sensors varying between 0.8563 and 0.9998, including three sensors having $r^2$ values greater than 0.9990. Exact values for the average thickness of the flux limiting layer were difficult to determine due to inconsistencies in membrane thickness achieved using the dipping technique.

Figure 6:
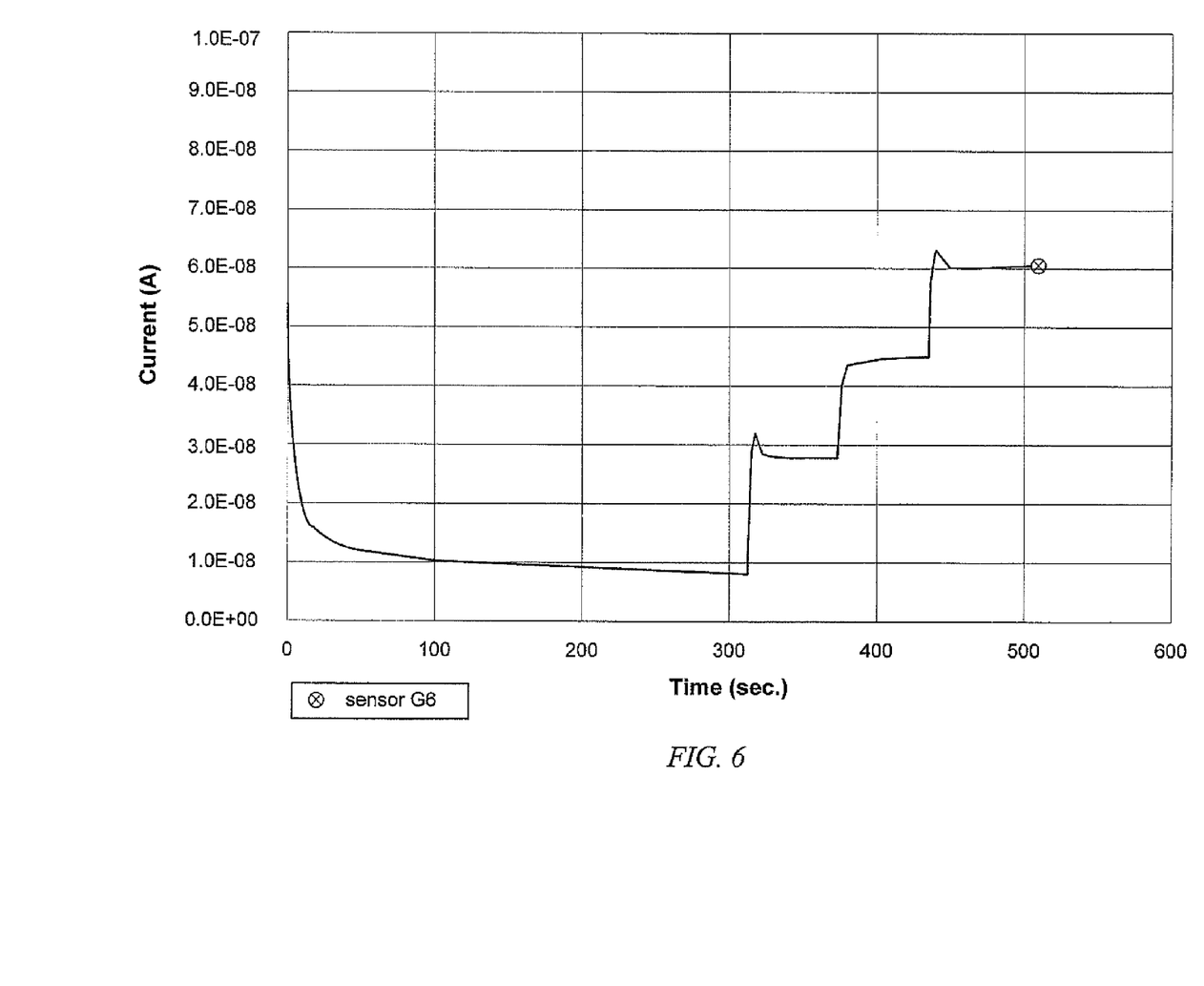
FIG. 6 is a graph of glucose assay results of the current output over time covering multiple step changes in glucose concentration, for a biosensor formed with flux limiting membranes according to an embodiment of the invention.

The graph of FIG. 6 shows a plot of the results of the glucose assay on sensor G6 as a function of current output over time. For simplicity, FIG. 6 includes only the curve for sensor G6 as being representative of the behavior of all eight sensors. The time period shown covers the three step changes in glucose concentration that correspond to the 50, 100, and 150 mg/dL concentrations. These step changes occurred at about 310, 372, and 432 seconds, respectively. As shown in the plot, after an initial transient spike in the current signal coincident with each step change, the response at each concentration quickly levels off to a steady state response. The linearity of this response over time for different glucose concentrations indicates that the flux limiting membrane is able to pass a proper oxygen-to-glucose ratio for a wide range of blood glucose concentrations. Similar qualitative behavior was observed in the other prototype sensors.

Additional tests were performed on sensor populations using a method for spray-coating EVA polymer dissolved in paraxylene to achieve superior control over membrane thickness. Based on studies conducted by the present inventor, spray-coating EVA in paraxylene has been shown to provide a consistent and uniform membrane layer that adheres to the polyimide substrate of the sensor. Paraxylene was selected as a solvent for its effectiveness in spray-coating applications. Paraxylene has been commonly used in electronics, for example, in low pressure vapor deposition processes forming a thin conformal coating on printed circuit boards. Paraxylene has a boiling point in a range that allows for effective evaporation for spraying, but prevents overly rapid evaporation that could cause clogging of the spray nozzle. Once deposited, the evaporation time of paraxylene allows for reasonably short drying times. In addition, paraxylene has certain adhesion promoting properties that facilitate bonding to the sensor substrate that is based upon a polymer. As a spray, it lends itself for application to the substrate of a very small flex circuit on which, in one embodiment, the working electrode may be effectively mounted for intravenous use.

Using 0.5 wt % to 6.0 wt % EVA-40 dissolved in paraxylene, an EVA solution was created and sprayed on working electrodes, and cured, to form the desired flux limiting membrane. Glucose assays were performed in the manner previously described. The results indicated that good linearity may be achieved by forming the flux limiting membrane from about 4 or 5 layers of sprayed-on EVA solution, where each layer is about 1 micron in thickness. Final membrane thickness may be process-dependent, since the spray method may deposit layers of varying porosities, i.e. surface areas having different flatness qualities or average depth of interstices. Thus, the number of layers needed for good linearity depends on the EVA formulation used, and on the process used for applying the spray. It has been found, however, that linear sensors may be manufactured by producing an average membrane thickness, a.k.a. diffusion layer thickness, between about 0.5 microns and about 10 microns. A preferred range for thickness may be between about 4 microns and about 6 microns, so that a sufficient amount of material may be deposited to withstand the mechanical stress of an intravenous insertion.

In the foregoing experiments, an EVA composition of 40 wt % (EVA-40) was used to create the solution that formed the flux limiting membranes. Membranes according to the invention, however, are not limited to this composition. Membranes may be formed using any EVA composition, for example, EVA having vinyl acetate compositions ranging from between about 9 wt % and about 50 wt %. As vinyl acetate is varied within the polyethylene content, solubility may also change (i.e. become less soluble at lower EVA compositions) and may not spray as effectively. A preferred range of EVA composition may be between about 25 wt % and about 40 wt % to promote good solubility and adhesion properties. The EVA may also be cross-linked to other polymers, such as poly(methylmethacrylate-co-butyl methacrylate), to create a different diffusion coefficient for glucose. The EVA may also be cross-linked with other compounds such as diglycidil ether or a diisocyanate, for example, to allow lower compositions of EVA to be used or to achieve better spray-coating performance.

Spray coating a flux limiting membrane may be especially effective in improving quality control for mass-production of biosensors. For example, a production lot of about 50 to 100 biosensors may be formed from a common flex circuit substrate. During fabrication, a step may be performed for spray-coating an EVA solution on the common substrate. After curing, the substrate may be cut or sliced into multiple, uniform strips to allow the flux limiting membrane of each biosensor to have approximately the same thickness.

Figure 7:
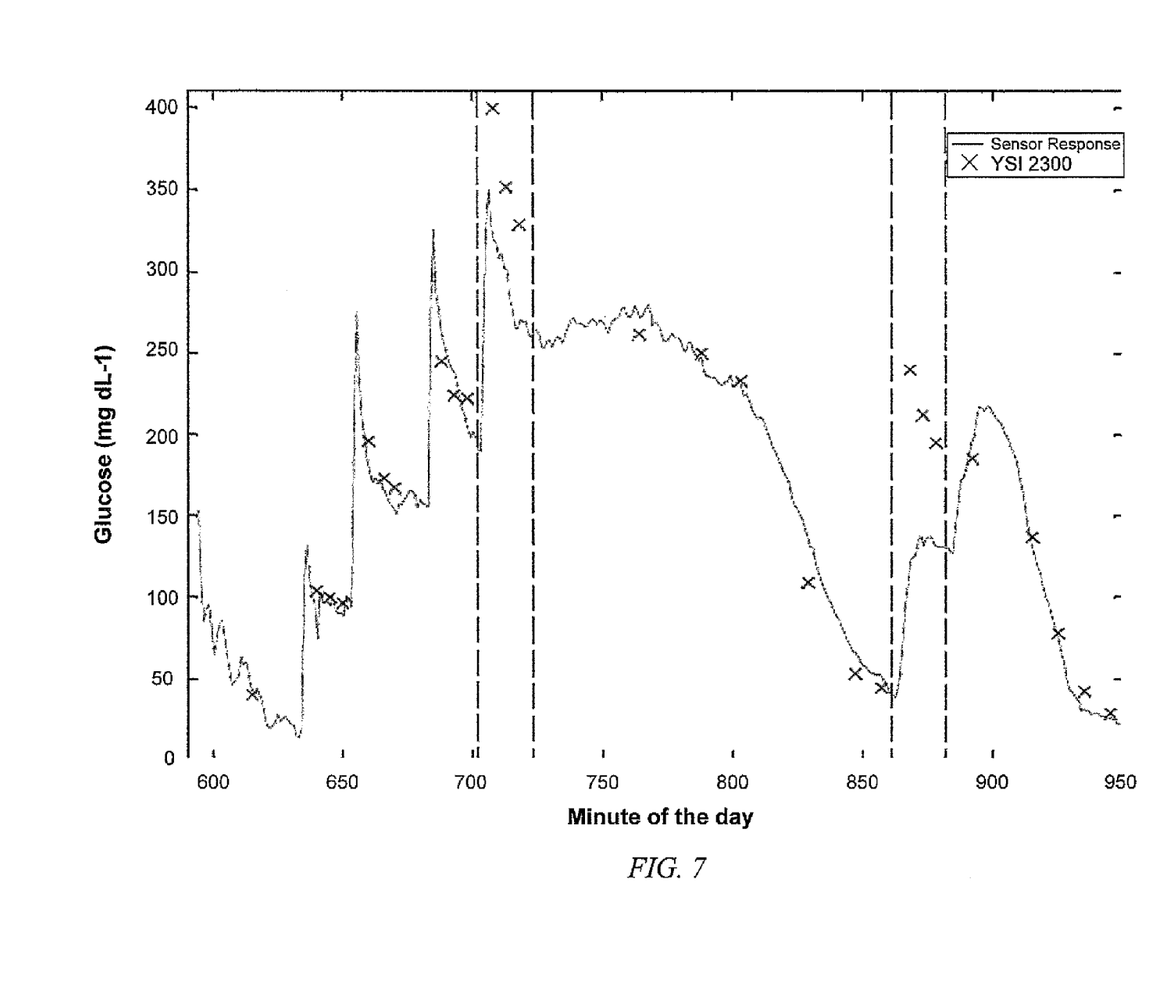
FIG. 7 shows results of an acute in vivo swine test for response of a glucose sensor having a flux limiting membrane according to an embodiment of the invention.

To test the biocompatibility and mechanical strength of a flux limiting membrane, an acute study was performed as an in vivo test on a swine. A prototype sensor was manufactured according to method 400 and then installed intravenously by mounting it in one lumen of a catheter that was inserted in a jugular vein of the swine using an over-the-wire technique. Glucose was periodically injected into the swine at a different entry site over a 6 hour period. The current output of the sensor was monitored during this period. Glucose concentration was also measured at periodic intervals over the same duration, by drawing blood samples and determining glucose concentration using a YSI 2300 glucose analyzer. The blood samples were drawn from a different lumen of the same catheter.

FIG. 7 shows the results of the swine test. With the exception of two transient periods between time 700-720 minutes and 860-880 minutes, the results show that in the early stages of the test, at time periods 600 through 700 minutes, the sensor readings agreed very well with the results of the reference standard. After the non-agreement interval at 860 minutes, it was discovered that the electrode was pressed against a vessel wall. Upon repositioning the catheter, the response was once again in good agreement with the YSI 2300 analyzer. Near the conclusion of the test period, at times 900 through 950 minutes, the readings still agreed, without any significant deviations. The consistent performance over a prolonged test period indicates no detachment of the flux limiting membrane, and no protein build-up, blood clotting, or other biofouling that would degrade the performance of the sensor over time. The transient portions may be explained as excursions where some non-linearity or other instability is experienced during abnormally high glucose levels or positioning difficulty with the catheter.

The foregoing disclosure and experimental test results demonstrate the efficacy of using EVA polymer to form a flux limiting membrane. In the particular case of a glucose sensor, EVA has the correct adhesion properties, biocompatibility properties, solubility suitable for spray-coating, and hydrophobic/hydrophilic properties to create a flux differential between glucose and oxygen to enable a sensor to exhibit a linear glucose response. In sum, EVA has been found to possess the proper material, chemical, performance, and manufacturing properties for forming a flux limiting membrane on an intravenous amperometric biosensor.

The invention has been disclosed in an illustrative manner. Accordingly, the terminology employed throughout should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A flux limiting membrane for an intravenous amperometric biosensor, comprising:
    an ethylene vinylacetate (EVA) polymer at least partially coating a glucose oxidase reagent, wherein the glucose oxidase reagent is disposed on an electrode of the biosensor wherein the ethylene vinylacetate polymer comprising hydrophilic segments selectively limiting diffusion of glucose from circulating intravenous blood to the glucose oxidase reagent,
    wherein the EVA composition has a vinyl acetate content between about 9 wt % and about 50 wt %.

2. The flux limiting membrane of claim 1, wherein the reactant comprises glucose.

3. The flux limiting membrane of claim 1, wherein the EVA polymer comprises an average diffusion layer thickness between about 0.5 microns and about 10 microns.

4. The flux limiting membrane of claim 1, further comprising a biocompatibility layer.

5. The flux limiting membrane of claim 4, wherein the biocompatibility layer comprises heparin.

6. The flux limiting membrane of claim 1, further comprising poly(methylmethacrylate-co-butyl methacrylate) blended with the EVA polymer.

7. The flux limiting membrane of claim 1, wherein the EVA polymer is cross-linked with diglycidil ether.

8. The flux-limiting membrane of claim 1, wherein the EVA polymer is cross-linked with a diisocyanate.

9. An intravenous amperometric biosensor, comprising:
    a flexible dielectric substrate;
    a reference electrode, a counter electrode, and working electrode bonded to the substrate;
    a glucose oxidase reagent layer disposed on the working electrode; and
    an ethylene vinylacetate (EVA) flux limiting membrane at least partially coating the glucose oxidase reagent layer and working electrode, wherein the EVA flux limiting membrane comprises hydrophilic segments selectively limiting diffusion of glucose from circulating intravenous blood to the glucose oxidase reagent,
    wherein the EVA composition has a vinyl acetate content between about 9 wt. % and about 40 wt %.

10. The biosensor of claim 9, wherein the EVA flux limiting membrane adheres to a portion of the electrode.

11. The biosensor of claim 9, wherein the EVA flux limiting membrane seals the glucose oxidase reagent layer and the electrode to the substrate.

12. The biosensor of claim 9, wherein the EVA flux limiting membrane comprises an average diffusion layer thickness between about 0.5 microns and about 10 microns.

13. The biosensor of claim 9, further comprising poly (methylmethacrylate-co-butyl methacrylate) blended with the EVA flux limiting membrane.

14. The biosensor of claim 9, wherein the EVA flux limiting membrane is cross-linked with diglycidil ether.

15. The biosensor of claim 9, wherein the EVA flux limiting membrane is cross-linked with a diisocyanate.

16. A flux limiting membrane comprising:
an ethylene vinylacetate (EVA) polymer bound to an enzyme electrode configured for intravenous positioning, the ethylene vinylacetate (EVA) polymer having a generally hydrophobic property to diffuse oxygen and sufficient hydrophilic segments to selectively limit glucose transport from circulating venous blood to an intravenously positioned enzyme electrode, the ethylene vinylacetate (EVA) polymer membrane comprising a vinyl acetate content between about 9 wt. % and about 40 wt. %.

17. The flux limiting membrane of claim 16, further comprising heparin.

18. The flux limiting membrane of claim 16, wherein the EVA polymer provides linearity of the current output vs. glucose concentration for the enzyme electrode.

19. A biosensor comprising:
an intravenous amperometric enzyme electrode bonded to a substrate; and an ethylene vinylacetate (EVA) polymer membrane at least partially coating the enzyme electrode and the substrate, the ethylene vinylacetate (EVA) comprising a vinyl acetate content between about 9 wt % and about 40 wt %;

wherein the ethylene vinylacetate (EVA) polymer membrane comprises a generally hydrophobic property to diffuse oxygen and sufficient hydrophilic segments to selectively limit glucose transport from circulating venous blood to the intravenously positioned enzyme electrode.

20. The biosensor of claim 19, wherein the EVA flux limiting polymer membrane seals the enzyme electrode to the substrate.

* * * * *